United States Patent [19]

Liauw et al.

[11] Patent Number: 4,582,850
[45] Date of Patent: Apr. 15, 1986

[54] TOPICAL AND SYSTEMIC TREATMENT OF PSORIASIS USING 7-CHLORO-N-(3,4-DICHLOROPHENYL)-2,3-DIHYDRO-5-HYDROXY-1-BENZOTHIEPIN-4-CARBOXAMIDE 1,1-DIOXIDE AND PHARMACEUTICALLY ACCEPTABLE SALTS THEREOF

[75] Inventors: Hui-Lian Liauw, Wycoff; Howard H. Oei, Basking Ridge; Edmond C. Ku, Upper Saddle River, all of N.J.

[73] Assignee: Ciba-Geigy Corporation, Ardsley, N.Y.

[21] Appl. No.: 706,563

[22] Filed: Feb. 28, 1985

[51] Int. Cl.$^4$ ............................................. A61K 31/38
[52] U.S. Cl. .................................................... 514/431
[58] Field of Search ........................................ 514/431

[56] References Cited

U.S. PATENT DOCUMENTS 4,185,109  1/1980  Rosen ................................. 514/431

Primary Examiner—Stanley J. Friedman
Attorney, Agent, or Firm—Michael W. Glynn

[57] ABSTRACT

Psoriasis is treated by the topical or oral administration of an effective endogenous lipoxygenase inhibiting amount of a compound of the formula

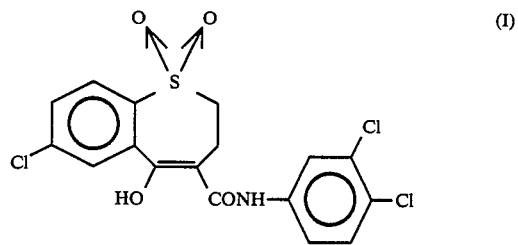

and the pharmaceutically acceptable salts thereof to a patient in need of the same.

6 Claims, No Drawings

TOPICAL AND SYSTEMIC TREATMENT OF PSORIASIS USING 7-CHLORO-N-(3,4-DICHLOROPHENYL)-2,3-DIHYDRO-5-HYDROXY-1-BENZOTHIEPIN-4-CARBOXAMIDE 1,1-DIOXIDE AND PHARMACEUTICALLY ACCEPTABLE SALTS THEREOF

Psoriasis is treated in accordance with the instant invention by the topical or oral adminitration of 7-chloro-N-(3,4-dichlorophenyl)-2,3-dihydro-5-hydroxy-1-benzothiepin-4-carboxamide-1,1-dioxide or a pharmaceutically acceptable salt thereof, in an amount sufficient to inhibit endogenous lipoxygenase present in psoriatic plaque fluid of a patient in need of the same.

7-Chloro-N-(3,4-dichlorophenyl)-2,3-dihydro-5-hydroxy-1-benzothiepin-4-carboxamide-1,1-dioxide of the formula I

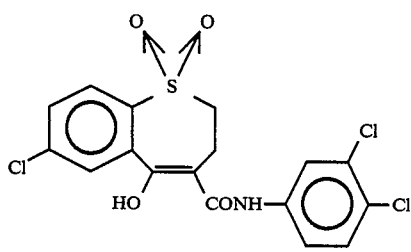

and the pharmaceutically acceptable salts thereof, are known and disclosed in U.S. Pat. No. 4,185,109, issued Jan. 22, 1980. This patent discloses such compounds as useful antiinflammatory agents, for example, in the treatment or management of arthritic conditions, and dermato-pathologic conditions of the type associated with inflammation, *inter alia*, as determined by carrageenin paw-edema screening tests. Aspirin, a widely prescribed and well known antiinflammatory agent, is similarly indicated for the treatment of arthritic conditions and dermato-pathologic conditions of the type associated with a positive response in standard carrageenin paw-edema screening tests. Aspirin and the compounds of U.S. Pat. No. 4,185,109 both inhibit the cyclooxygenase pathway. Inhibition of the cyclooxygenase pathway also occurs in psoriatic lesions which causes the deposition of arachidonic acid to be redirected via the 5- and 12-lipoxygenase pathways. The transformation of arachidonic acid to $LTB_4$ and 5-HETE in the epidermis is catalyzed by the 5- and 12-lipoxygenases. Thus, high levels of arachidonic acid and 5-HETE is associated with psoriasis. Aspirin, which acts to inhibit the cyclooxygenase pathway, is known to exacerbate psoriasis. Unexpectedly and surprisingly, it has been found that the compound of formula I and its salts, while they, like aspirin, likewise inhibit cyclooxygenase, also act as lipoxygenase inhibitors. The compound of formula I and salts thereof, in contradistinction to aspirin, effectively interfere with the synthesis of arachidonic acid to $LTB_4$ and 5-HETE as a result of such lipoxygenase inhibition, and are accordingly highly valuable in the treatment of psoriasis.

Suitable pharmaceutically acceptable salts of the compound of formula I include the sodium, potassium, ammonium, mono-, di- or trimethyl- or -ethylammonium, ethanolammonium, diethanolammonium, triethanolammonium, glucamine, pyrrolidinium, piperidinium or morpholinium salt thereof. One especially preferred salt is the sodium monohydrate of the compound of formula I, also known as enolicam sodium.

The compound of formula I and its salts can be administered orally in the form of capsules, tablets, solutions or suspensions, and if desired, together with pharmaceutically acceptable excipients. Preferred are tablets and gelatin capsules comprising the active ingredient together with one or more excipients, including (a) diluents, e.g. lactose, dextrose, surcrose, mannitol, sorbitol, cellulose and/or glycine, (b) lubrients, e.g. silica, stearic acid, magnesium or calcium stearate and/or polyethyleneglycol, (c) binders, e.g. magnesium aluminum silicate, starch paste, gelatin, tragacanth, methylcellulose, sodium carboxymethylcellulose and/or polyvinylpyrrolidone, (d) disintegrants, e.g. starches, agar, alginic acid or its sodium salt, enzymes of the binders, or effervescent mixtures and/or (e) absorbents, colorants, flavors and sweeteners.

The compound of formula I and its salts can alternatively be administered topically in the form of a solution, suspension, ointment or cream, together with pharmacetucially acceptable excipients. Preferred are ointments and creams comprising the active ingredient together with one or more exipients including (a) diluents, e.g. water, glycerine, petroleum jelly, alcohols, including ethanol, propylene glycol, fats and oils such as coconut oil, aliphatic ethers and/or esters, (b) stabilizers, emulsifiers and/or colloids, such as polyvinylalcohol, fatty acid salts, polyethoxylated fatty oils and the like, (c) thickeners, such as starch, gelatin, or polyalkylene glycols, and the like, (d) skin penetrants, such as caprolactam, fluorinated lower alkanols and the like, and/or (e) colorants, perfumes and/or emollients.

For oral administration, the applied dosage of the active ingredient of formula I and it salts may range between about 1 to about 50 mg/kg/day, preferably between about 1 to about 25 mg/kg/day, advantageously between about 5 to about 20 mg/kg/day.

For topical administration, the applied dosage of the active ingredient of formula I and its salts is such that the solution, suspension, ointment or cream is present in an amount between about 0.1 to about 20 weight percent of the formulation, preferably between about 0.1 to about 10 weight percent of the formulation. The resulting formulation is applied directly to the affected skin by topical application.

What is claimed is:

1. A method of treating a patient suffering from psoriasis comprising the oral or topical administration of an effective endogenous lipoxygenase inhibiting amount of a compound of the formula

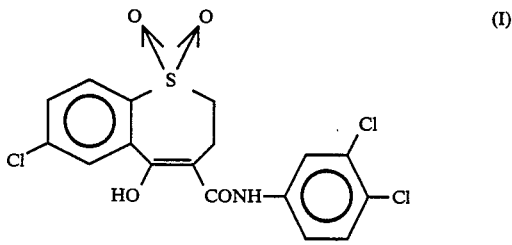

or a pharmaceutically acceptable salt thereof, to said patient in need of the same.

2. A method according to claim 1, wherein said administration is oral.

3. A method according to claim 1, wherein said administration is topical.

4. A method according to claim 1, wherein said compound is in the form of its sodium salt.

5. A method according to claim 2, wherein said compound is in the form of its sodium salt.

6. A method according to claim 3, wherein said compound is in the form of its sodium salt.

* * * * *